US011883048B2

(12) United States Patent
Akbarian et al.

(10) Patent No.: US 11,883,048 B2
(45) Date of Patent: Jan. 30, 2024

(54) INSTRUMENT WITH INTEGRAL IMAGING AND IRRIGATION FEATURES

(71) Applicants: Acclarent, Inc., Irvine, CA (US);
Biosense Webster (Israel) Ltd.,
Yokneam (IL)

(72) Inventors: Fatemeh Akbarian, Rancho Palos Verdes, CA (US); Yehuda Algawi, Binyamina (IL); Itzhak Fang, Irvine, CA (US); Jetmir Palushi, Irvine, CA (US); Athanasios Papadakis, Newport Beach, CA (US); Henry F. Salazar, Pico Rivera, CA (US); Ehsan Shameli, Irvine, CA (US)

(73) Assignees: Acclarent, Inc., Irvine, CA (US);
Biosense Webster (Israel) Ltd.,
Yokneam (IL)

( * ) Notice: Subject to any disclaimer, the term of this patent is extended or adjusted under 35 U.S.C. 154(b) by 807 days.

(21) Appl. No.: 16/697,740

(22) Filed: Nov. 27, 2019

(65) Prior Publication Data

US 2020/0178775 A1    Jun. 11, 2020

Related U.S. Application Data

(60) Provisional application No. 62/776,718, filed on Dec. 7, 2018.

(51) Int. Cl.
*A61B 17/24*    (2006.01)
*A61B 1/01*    (2006.01)
(Continued)

(52) U.S. Cl.
CPC ............ *A61B 17/24* (2013.01); *A61B 1/0051* (2013.01); *A61B 1/00094* (2013.01); *A61B 1/01* (2013.01);
(Continued)

(58) Field of Classification Search
CPC ............ A61B 1/00082; A61B 1/00094; A61B 1/00098; A61B 1/00135; A61B 1/0051;
(Continued)

(56) References Cited

U.S. PATENT DOCUMENTS 9,155,492 B2    10/2015    Jenkins et al.
10,561,370 B2    2/2020    Salazar et al.
(Continued)

FOREIGN PATENT DOCUMENTS

CN    106943114 A    7/2017
EP    2502550 A2    9/2012
(Continued)

OTHER PUBLICATIONS

International Search Report and Written Opinion dated Jun. 25, 2020 for International Application No. PCT/IB2019/060458, 20 pages.

(Continued)

*Primary Examiner* — Aaron B Fairchild
*Assistant Examiner* — Julianna J Nicolaus
(74) *Attorney, Agent, or Firm* — Frost Brown Todd LLP (57) ABSTRACT

A surgical instrument and related method includes an instrument body, a guide shaft distally projecting from the instrument body, and a first surgical tool. The guide shaft has a guide sidewall, a guide lumen, and a clearance opening radially extending through the guide sidewall in communication with the guide lumen. The first surgical tool has an elongate body and a distal head configured to deflect relative to the elongate body from a first position to a second position. The distal head in the first position is positioned within the guide lumen along the central axis. The distal head in the second position is deflected from the central axis and extends at least partially through the clearance opening (Continued)

thereby vacating at least a portion of the guide lumen for introducing a second surgical tool through the guide lumen.

18 Claims, 8 Drawing Sheets

(51) Int. Cl.
  *A61M 29/02*   (2006.01)
  *A61B 1/00*   (2006.01)
  *A61B 1/005*   (2006.01)
  *A61B 1/05*   (2006.01)
  *A61B 17/34*   (2006.01)
  *A61B 1/015*   (2006.01)
  *A61B 1/06*   (2006.01)
  *A61B 17/00*   (2006.01)

(52) U.S. Cl.
  CPC ............... *A61B 1/015* (2013.01); *A61B 1/05* (2013.01); *A61B 1/0676* (2013.01); *A61B 17/3415* (2013.01); *A61B 17/3417* (2013.01); *A61M 29/02* (2013.01); *A61B 1/0008* (2013.01); *A61B 2017/003* (2013.01); *A61B 2017/00296* (2013.01); *A61B 2017/3445* (2013.01); *A61B 2217/005* (2013.01); *A61B 2217/007* (2013.01); *A61M 2029/025* (2013.01)

(58) Field of Classification Search
  CPC ....... A61B 1/015; A61B 1/018; A61B 1/0676; A61B 2017/0034; A61B 2017/025; A61B 2017/3345; A61B 17/3417
  See application file for complete search history.

(56) References Cited

U.S. PATENT DOCUMENTS

| | | | |
|---|---|---|---|
| 2003/0187460 A1* | 10/2003 | Chin | A61B 17/3421 606/129 |
| 2006/0173244 A1* | 8/2006 | Boulais | A61B 1/015 600/156 |
| 2006/0211918 A1* | 9/2006 | Lieponis | A61B 1/07 600/128 |
| 2007/0249896 A1 | 10/2007 | Goldfarb et al. | |
| 2010/0274188 A1 | 10/2010 | Chang et al. | |
| 2011/0004057 A1 | 1/2011 | Goldfarb et al. | |
| 2012/0265017 A1* | 10/2012 | Meyer | G02B 23/2423 600/173 |
| 2013/0053645 A1* | 2/2013 | Weitzner | A61B 1/00142 600/176 |
| 2013/0274715 A1 | 10/2013 | Chan et al. | |
| 2014/0088371 A1* | 3/2014 | Vayser | A61M 1/74 600/249 |
| 2014/0364725 A1 | 12/2014 | Makower | |
| 2015/0038793 A1* | 2/2015 | Prior | A61M 5/329 600/204 |
| 2016/0081857 A1* | 3/2016 | Ha | A61B 1/00082 600/106 |
| 2016/0287055 A1* | 10/2016 | Kesten | A61B 17/29 |
| 2017/0007345 A1* | 1/2017 | Smith | A61B 1/018 |
| 2018/0206712 A1* | 7/2018 | Begg | A61B 1/00183 |
| 2019/0015645 A1 | 1/2019 | Matlock et al. | |
| 2019/0015646 A1 | 1/2019 | Matlock et al. | |
| 2020/0187751 A1* | 6/2020 | Zheng | A61B 1/00078 |
| 2020/0345224 A1* | 11/2020 | Begg | A61B 1/05 |

FOREIGN PATENT DOCUMENTS

| | | |
|---|---|---|
| JP | 2010-220665 A | 10/2010 |
| WO | WO 2015/110996 A1 | 7/2015 |
| WO | WO 2016/040237 A1 | 3/2016 |
| WO | WO 2016/138128 A1 | 9/2016 |

OTHER PUBLICATIONS

Japanese Notification of Reasons for Refusal dated Aug. 29, 2023, for Application No. 2021-532017, 6 pages.

* cited by examiner

INSTRUMENT WITH INTEGRAL IMAGING AND IRRIGATION FEATURES

CROSS-REFERENCE TO RELATED APPLICATION

This application claims the benefit of U.S. Provisional Pat. App. No. 62/776,718, entitled "Instrument with Integral Imaging and Irrigation Features," filed on Dec. 7, 2018, the disclosure of which is hereby incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty System by Acclarent, Inc. of Irvine, California.

In the context of Eustachian tube dilation, a dilation catheter or other dilation instrument may be inserted into the Eustachian tube and then be inflated or otherwise expanded to thereby dilate the Eustachian tube. The dilated Eustachian tube may provide improved ventilation from the nasopharynx to the middle ear and further provide improved drainage from the middle ear to the nasopharynx. Methods and devices for dilating the Eustachian tube are disclosed in U.S. Patent Pub. No. 2010/0274188, entitled "Method and System for Treating Target Tissue within the ET," published on Oct. 28, 2010, now abandoned, the disclosure of which is incorporated by reference herein; and U.S. Patent Pub. No. 2013/0274715, entitled "Method and System for Eustachian Tube Dilation," published on Oct. 17, 2013, now abandoned, the disclosure of which is incorporated by reference herein. An example of such a system is the Aera® Eustachian Tube Balloon Dilation System by Acclarent, Inc. of Irvine, California.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then be illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pat. No. 9,155,492, entitled "Sinus Illumination Lightwire Device," issued Oct. 13, 2015, the disclosure of which is incorporated by reference herein. An example of such an illuminating guidewire is the Relieva Luma Sentry® Sinus Illumination System by Acclarent, Inc. of Irvine, California.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation systems that may be used in IGS procedures is the CARTO® 3 System by Biosense-Webster, Inc., of Irvine, California. In some IGS procedures, a digital tomographic scan (e.g., CT or MM, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

An example of an electromagnetic IGS systems that may be used in ENT and sinus surgery is the CARTO® 3 System by Biosense-Webster, Inc., of Irvine, California. When applied to functional endoscopic sinus surgery (FESS), balloon sinuplasty, and/or other ENT procedures, the use of IGS systems allows the surgeon to achieve more precise movement and positioning of the surgical instruments than can be achieved by viewing through an endoscope alone. As a result, IGS systems may be particularly useful during performance of FESS, balloon sinuplasty, and/or other ENT procedures where anatomical landmarks are not present or are difficult to visualize endoscopically. Examples of use of an IGS system in an ENT procedure are described in U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein; and U.S. patent application Ser. No. 15/933,737, entitled "Apparatus to Secure Field Generating Device to Chair," filed Mar. 23, 2018, issued as U.S. Pat. No. 10,561,370 on Dec. 8, 2020, the disclosure of which is incorporated by reference herein.

It may be desirable to provide easily controlled placement of a balloon of a dilation catheter in an anatomical passageway, including in procedures that will be performed only by a single operator. While several systems and methods have been made and used to position a balloon of a dilation catheter in an anatomical passageway, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms are also are used herein. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Dilation Instrument

A. Overview

FIGS. 1A-1D show an exemplary dilation instrument (10) that may be used to dilate the ostium of a paranasal sinus, to dilate another passageway associated with drainage of a paranasal sinus, to dilate a Eustachian tube, or to dilate some other anatomical passageway (e.g., within the ear, nose, or throat, etc.). As will be described in greater detail below, dilation instrument (10) of the present example provides adjustability that enables the operator to use dilation instrument (10) in different scenarios, without requiring the operator to switch between different instruments. For instance, dilation instrument (10) may be used to dilate various different anatomical passageways (e.g., frontal sinus ostium, frontal recess, maxillary sinus ostium, sphenoid sinus ostium, ethmoid sinus ostium, Eustachian tube, etc.) by making simple adjustments to structural features of the instrument.

Dilation instrument (10) of this example includes a handle assembly (12), a guide shaft assembly (14) extending distally from handle assembly (12); a guidewire actuation assembly (16) slidably coupled with handle assembly (12); and a dilation catheter actuation assembly (18) slidably coupled with handle assembly (12). A guidewire module (20) is coupled with a guidewire (22) of dilation instrument (10) via a connector (24). An inflation fluid source (26) and an irrigation fluid source (28) are coupled with a dilation catheter (30) of dilation instrument (10) via a connector (32). A suction source (34) is coupled with a suction conduit (not shown) of dilation instrument (10) via a suction port (36).

Figure 1A:
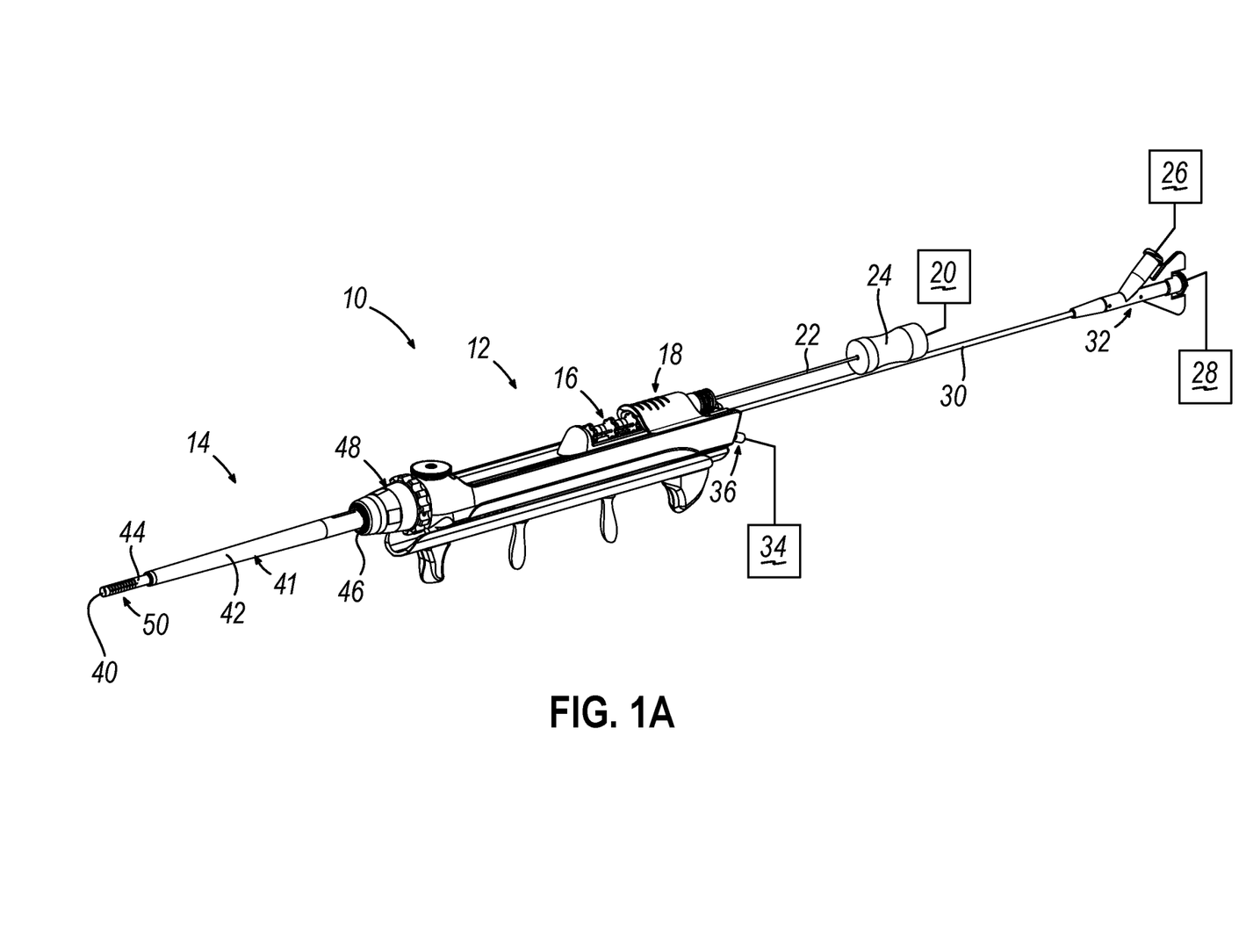
FIG. 1A depicts a perspective view of an exemplary dilation instrument, with a guidewire and a dilation catheter each in respective proximal positions.
Figure 1B:
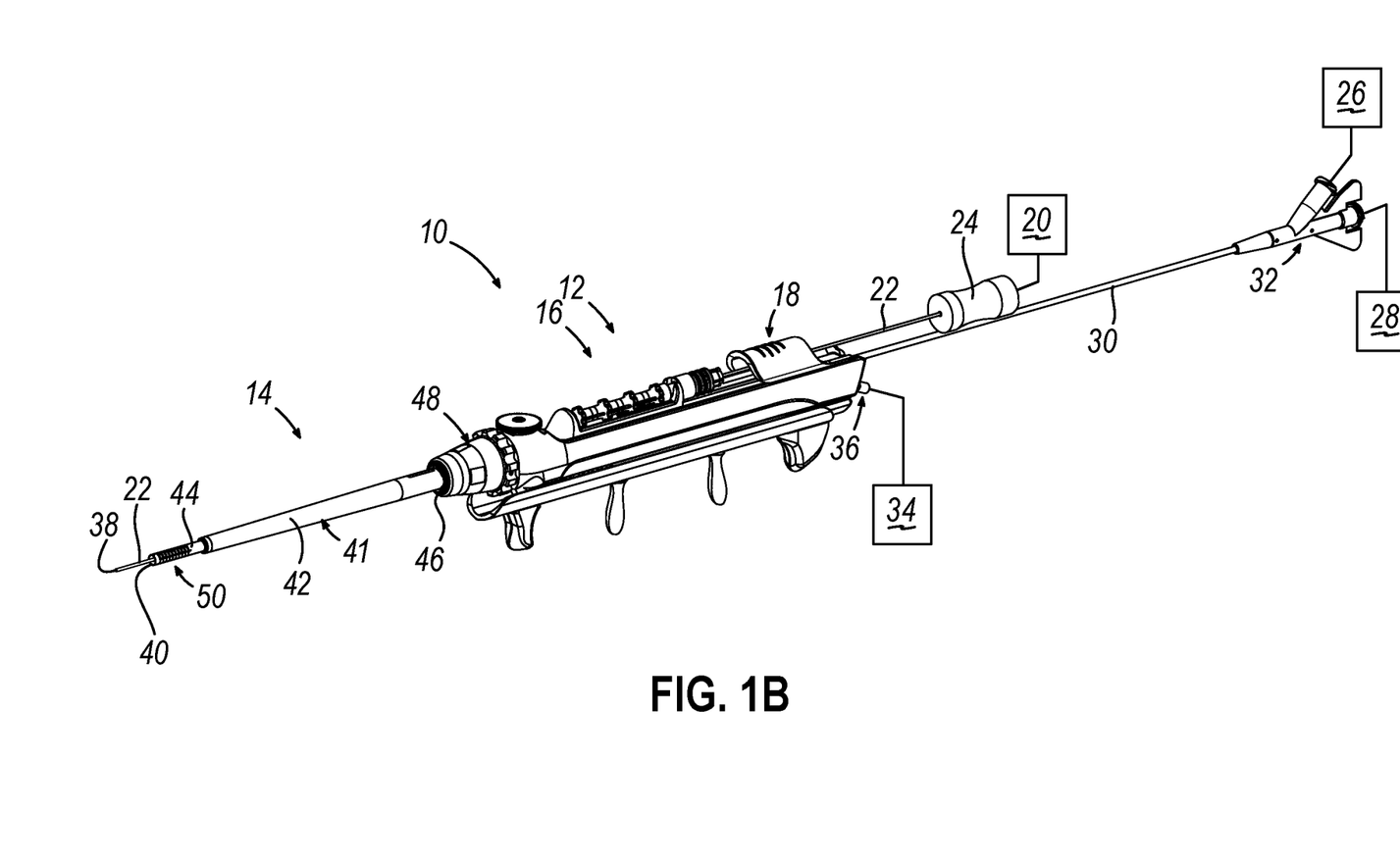
FIG. 1B depicts a perspective view of the dilation instrument of FIG. 1A, with the guidewire in a distal position and the dilation catheter in the proximal position.
Figure 1C:
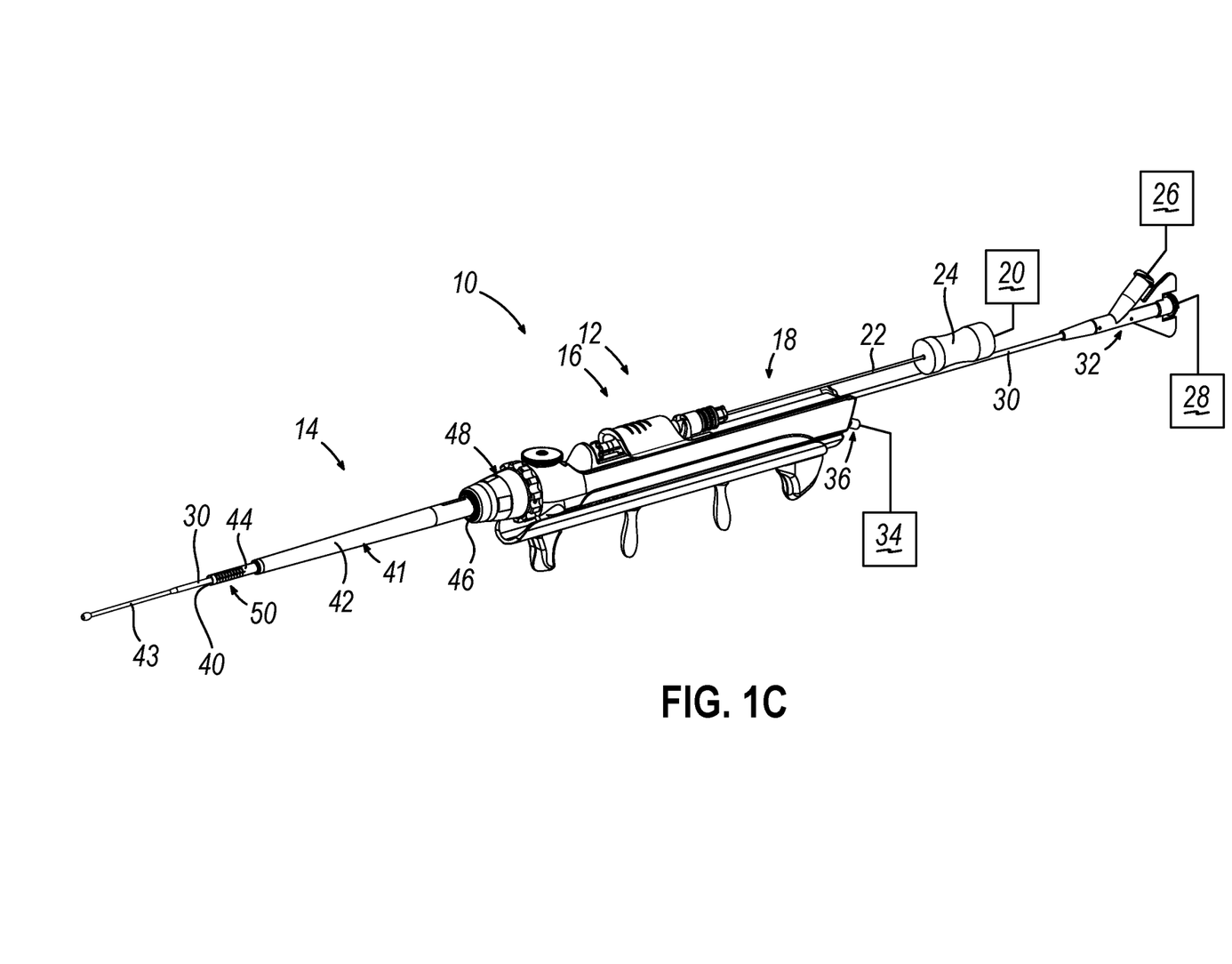
FIG. 1C depicts a perspective view of the dilation instrument of FIG. 1A, with the guidewire and the dilation catheter each in respective distal positions, and with a dilator of the dilation catheter in a non-expanded state.
Figure 1D:
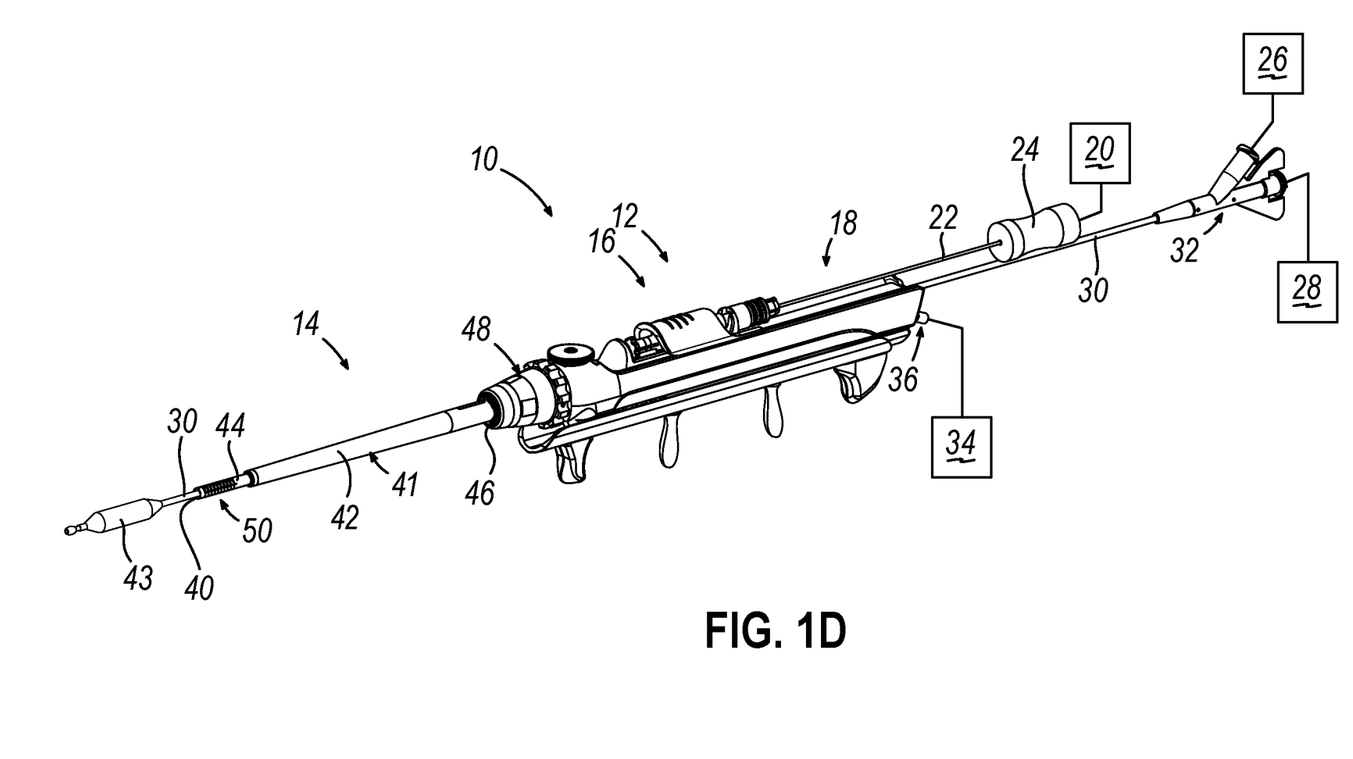
FIG. 1D depicts a perspective view of the dilation instrument of FIG. 1A, with the guidewire and the dilation catheter each in respective distal positions, and with a dilator of the dilation catheter in an expanded state.

Handle assembly (12) is sized and configured to be grasped and operated by a single hand of an operator. The operator may selectively operate guidewire actuation assembly (16) and dilation catheter actuation assembly (18) with the same single hand that grasps handle assembly (12). As shown in the transition from FIG. 1A to FIG. 1B, the operator may advance guidewire actuation assembly (16) distally along handle assembly (12) to thereby advance guidewire (22) distally, such that a distal end (38) of guidewire (22) is positioned distal to a distal guide end (40) of guide shaft assembly (14). As shown in the transition from FIG. 1B to FIG. 1C, the operator may advance dilation catheter actuation assembly (18) distally along handle assembly (12) to thereby advance dilation catheter (30) distally, such that a distal tip of dilation catheter (30) is positioned distal to the distal end of guide shaft assembly (14). With dilation catheter (30) advanced to a distal position, the operator may then inflate a dilator (43) of dilation catheter (30) to achieve an expanded state as shown in FIG. 1D, to thereby dilate an anatomical passageway in which dilator (43) is positioned.

In the present example, dilation catheter (30) is coaxially disposed within guide shaft assembly (14), and guidewire (22) is coaxially disposed within dilation catheter (30). In some other versions, guide shaft assembly (14) is coaxially disposed within dilation catheter (30), and guidewire (22) is coaxially disposed within guide shaft assembly (14). Also in some versions, guidewire (22) is omitted.

Examples of features and functionalities of the above-noted components of dilation instrument (10) are described in greater detail below. These features and functionalities are merely illustrative examples. By way of further example only, the features and functionalities described herein may be modified in accordance with the teachings of U.S. patent application Ser. No. 16/032,471, entitled "Adjustable Instrument for Dilation of Anatomical Passageway," filed on Jul. 11, 2018, issued as U.S. Pat. No. 10,874,839 on Dec. 29, 2020, as well as U.S. patent application Ser. No. 16/032,489, entitled "Adjustable Instrument for Dilation of Anatomical Passageway," filed on Jul. 11, 2018, issued as U.S. Pat. No. 11,027,105 on Jun. 8, 2021, the disclosures of which are hereby incorporated by reference herein. Other variations of the features and functionalities described herein will be apparent to those skilled in the art in view of the teachings herein.

B. Exemplary Guide Shaft Assembly and Associated Actuation Assemblies

Figure 2A:
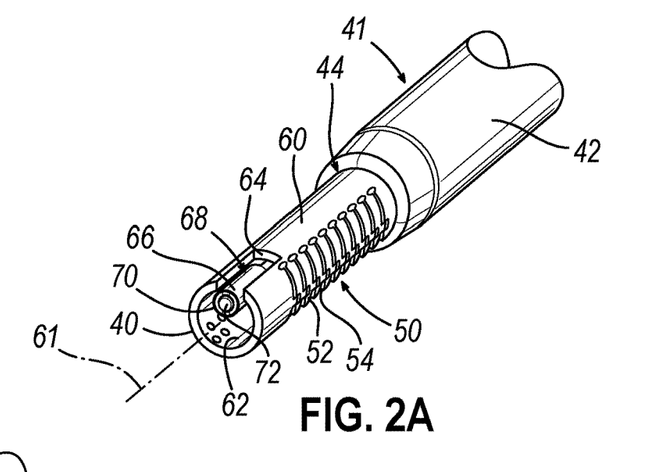
FIG. 2A depicts an enlarged perspective view of the dilation instrument of FIG. 1A having a clearance shaft defining a guide lumen and a clearance opening and a first exemplary endoscope positioned within the guide lumen in a distal facing use position.

FIG. 2A shows guide shaft assembly (14) of this example has a guide clearance shaft (41) including a rigid shaft member (42) and a flexible shaft member (44) distally extending to distal guide end (40). Guide shaft assembly (14) further includes a push-pull wire (not shown), a cam barrel (46) (see FIG. 1D), and a deflection control knob (48) (see FIG. 1D). Shaft members (42, 44), cam barrel (46) (see FIG. 1D), and deflection control knob (48) (see FIG. 1D) are coaxially aligned with each other in this example, with push-pull wire (not shown) being laterally offset from the central longitudinal axis shared by shaft members (42, 44), cam barrel (46) (see FIG. 1D), and deflection control knob (48) (see FIG. 1D). Guide shaft assembly (14) is operable to guide guidewire (22) and dilation catheter (30) along an operator-selected exit angle relative to the central longitudinal axis of guide shaft assembly (14).

In some versions, both shaft members (42, 44) are formed of a metallic material, such as stainless steel and/or nitinol. In some such versions, shaft members (42, 44) (and at least some other portions of instrument (10)) may be reusable, with such reusable components being subject to cleaning and sterilization between uses on different patients. In some other versions, one or both of shaft members (42, 44) may be formed of a polymeric material. In some such versions, shaft members (42, 44) may be treated as single-use-only components. Flexible shaft member (44) is secured to rigid shaft member (42) and is positioned distally in relation to rigid shaft member (42). Flexible shaft member (44) includes a flex section (50) that is formed by a series of ribs (52), which are separated by a series of notches (54). Notches (54) are generally V-shaped, with a circular opening at the vertex of each "V." Notches (54) also include tab portions (56) (see FIG. 3A) that respectively fit in a plurality of corresponding sub-notches (58) (see FIG. 3A). Thereby, flex section (50) is configured to distally and linearly extend in a straight configuration as well as arcuately deflect to a fully bent configuration as selectively directed via push-pull wire (not shown) in shaft members (42, 44) to provide controlled bending of flex section (50).

C. Exemplary Clearance Shaft and Instrument Arrangement for Concurrently Accommodating a Dilation Catheter With respect to FIGS. 2A-2B, guide clearance shaft (41) of the present example includes flexible shaft member (44) having a guide sidewall (60) surrounding a central axis (61) and defining a guide lumen (62), distal guide end (40), and a clearance opening (64) extending through guide sidewall (60) in communication with guide lumen (62). Clearance opening (64) is configured to receive a surgical instrument therethrough such that at least a portion of the surgical instrument vacates guide lumen (62) to concurrently accommodate another surgical instrument passing thereby. More particularly, clearance opening (64) is configured to receive a distal head (66) of an endoscope (68) while dilation catheter (30) passes radially alongside distal head (66) when longitudinally aligned with distal head (66). While endoscope (68) is shown in the present example, any such surgical tool having a relatively large distal portion sized to fit through clearance opening (64) and a relatively smaller proximal portion may be similarly used. To this end, the invention is not intended to be unnecessarily limited to the particular endoscope (68) shown in the present example.

As shown in the present example, distal head (66) of endoscope (68) distally extends to a distal end face (70) having a co-axially positioned camera (72) positioned thereon. In addition, a suction opening (74) of a suction conduit (not shown) is positioned on distal end face (70) at one side lateral of camera (72), whereas an irrigation opening (76) of an irrigation conduit (not shown) is positioned on distal end face (70) at another, opposite lateral side of camera (72). Suction opening (74) and irrigation opening (76) are each generally crescent shape and collectively have a generally annular shape surrounding camera (72), although each are fluidly sealed from each other. An annular light source (78) surrounds camera (72) and suction and irrigation openings (74, 76) at a fillet edge around distal end face (70).

An elongate endoscope body (80) proximally extends from distal head (66) and includes suction and irrigation conduits (not shown) proximally extending therethrough as well as various wires (not shown) communicating power and/or data with light source (78) and camera (72). Elongate endoscope body (80) of the present example has a sidewall that envelops suction and irrigation conduits (not shown) and wires (not shown) such that neither suction and irrigation conduits (not shown) nor wires (not shown) are exposed within guide lumen (62). In another example, an alternative endoscope body (not shown) does not include the sidewall. Rather, suction and irrigation conduits (not shown) as well as wires (not shown) of elongate endoscope body (not shown) proximally extend from distal head (66) through guide lumen (62) while exposed in guide lumen (62). The invention is thus not intended to be unnecessarily limited to the particular elongate endoscope body (80) with sidewall as shown and described herein.

Figure 2B:
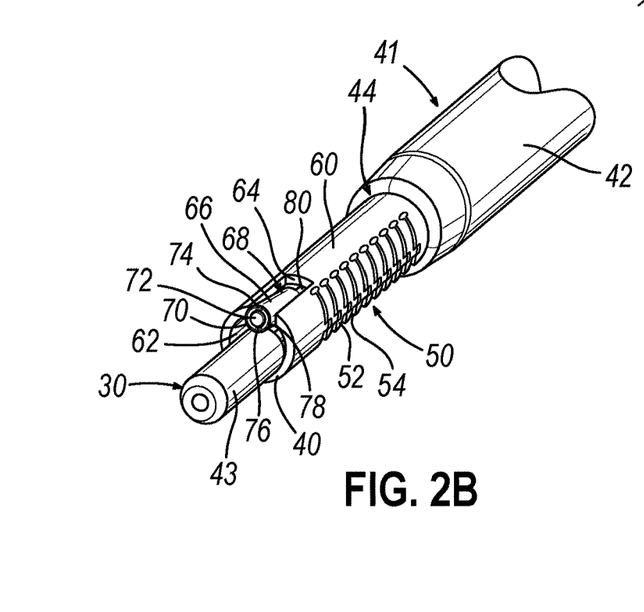
FIG. 2B depicts the enlarged perspective view of the dilation instrument similar to FIG. 2A, but showing a distal head of the endoscope in a deflected position extending through the clearance opening to concurrently accommodate an enlarged portion of a dilation catheter passing through the guide lumen.

Distal head (66) is configured to pivot relative to elongate endoscope body (80) from a distal facing use position as shown in FIG. 2A to a deflected position as shown in FIG. 2B. More particularly, distal head (66) is pivotally and resiliently secured to guide clearance shaft (41) adjacent to and longitudinally aligned with clearance opening (64) such that clearance opening (64) receives distal head (66) as distal head vacates guide lumen (62) and moves from the distal facing use position to the deflected position. As used herein in the present example, the term "distal facing use position" refers to camera (72) on distal end face (70) being generally transverse to central axis (61) and facing in a distal direction for use viewing an anatomy of the patient directly distal from distal guide end (40). In contrast, the term "deflected position" in the present position refers to camera (72) on distal end face (70) not being transverse with central axis (61) and facing another direction that is not directly distal from distal guide end (40). Such particular orientations of camera (72) for use and as deflected may vary in alternative examples, and the invention is not intended to be unnecessarily limited to the particular distal facing use position and deflected position of the present example.

In addition, distal head (66) is secured at a longitudinal position distal from flex section (50) and diametrically opposed from notches (54) and push-pull wire (not shown). Distal head (66) thus laterally deflects along with a remainder of guide sidewall (60) distal of flex section (50), including distal guide end (40). Distal head (66) remains longitudinally fixed relative to distal guide end (40) from the straight configuration throughout arcuate deflections to the fully bent configuration. To accommodate travel of distal head (66) throughout these various configurations, elongate endoscope body (80) with suction and irrigation conduits (not shown) and wires (not shown) translates back and forth through guide lumen (62) following with distal head (66). For example, from the straight configuration toward the fully bent configurations, elongate endoscope body (80) with suction and irrigation conduits (not shown) and wires (not shown) distally translates to remain connected to distal head (66) for further use.

Distal guide end (40) defines an outer profile surrounding central axis (61). In the distal facing use position, distal head (66) is radially contained within the outer profile. In contrast, distal head (66) in the deflected position radially extends beyond the outer profile of distal guide end (40) as shown in FIG. 2B in order to accommodate another surgical tool, such as dilation catheter (30) passing through guide lumen (62). To this end, dilation catheter (30) has dilator (43) and an elongate catheter body (84) proximally extending from dilator (43). Like endoscope (68), dilation catheter (30) has a relatively large distal portion, such as dilator (43), and a relatively smaller proximal portion, such as elongate catheter body (84) (see FIG. 2C). As discussed below in greater detail, dilator (43) is sized to radially fit alongside elongate endoscope body (80) within guide lumen (62), but does not radially fit alongside distal head (66) of endoscope (68) within guide lumen (62) unless distal head (66) at least partially vacates guide lumen (62) to accommodate dilator (43).

Figure 2C:
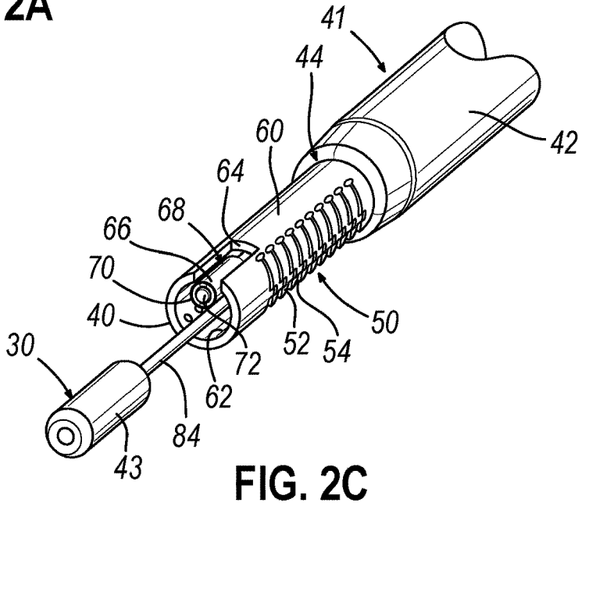
FIG. 2C depicts the enlarged perspective view of the dilation instrument similar to FIG. 2B, but showing the distal head of the endoscope returned from the deflected state to the distal facing use state after the enlarged portion of the dilation catheter has been distally positioned therefrom.

With respect to FIGS. 2B-2C, distally translating dilator (43) against a proximal portion of distal head (66) urges distal head (66) to pivot from the distal facing use position to the deflected position. Distal head (66) thus vacates a sufficient amount of guide lumen (62) through clearance opening (64) to allow dilator (43) to radially pass against distal head (66) toward a distal position for use. Once dilator (43) longitudinally passes beyond distal head (66), distal head (66) resiliently returns from the deflected position to the distal facing use position such that the operator may view dilator (43) during use within the patient. In the present example, clearance opening (64) distally extends through guide sidewall (60) to distal guide end (40) to accommodate pivotal movement of distal end face (70), which is shown as coplanar with distal guide end (40). Alternatively, distal end face (70) may be more proximally positioned from distal guide end (40). In another example, clearance opening (64) may similarly be more proximally positioned from distal guide end (40). The invention is thus not intended to be unnecessarily limited to one or both of distal end face (70) of distal head (66) or a distal terminal end of clearance opening (64) being in longitudinal alignment with distal guide end (40).

Figure 3A:
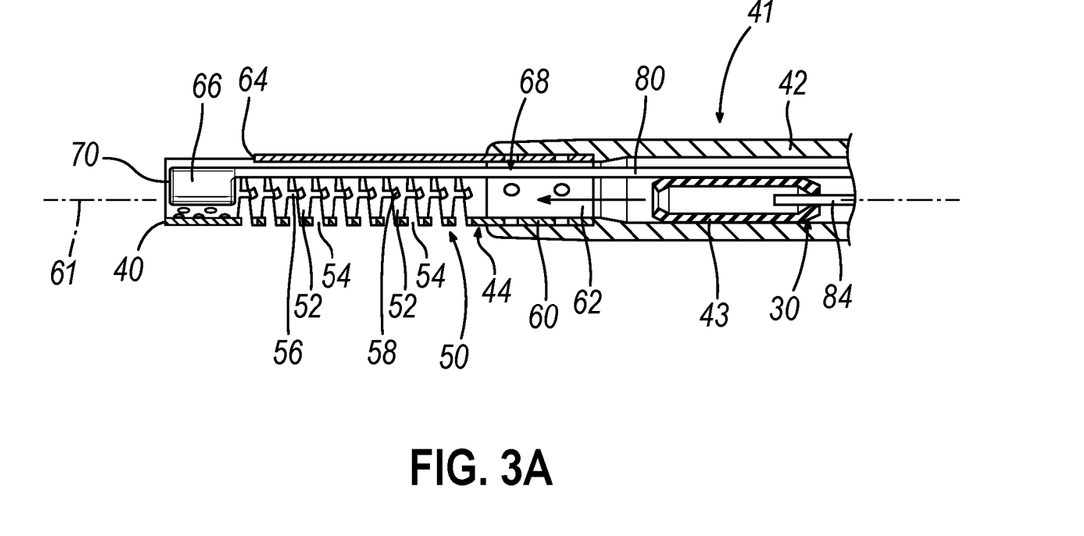
FIG. 3A depicts a cross-sectional view of the dilation instrument of FIG. 1A taken along a centerline thereof having the distal head of the endoscope in the distal facing use state within the guide lumen of the clearance shaft and the dilation catheter distally translating therethrough.
Figure 3B:
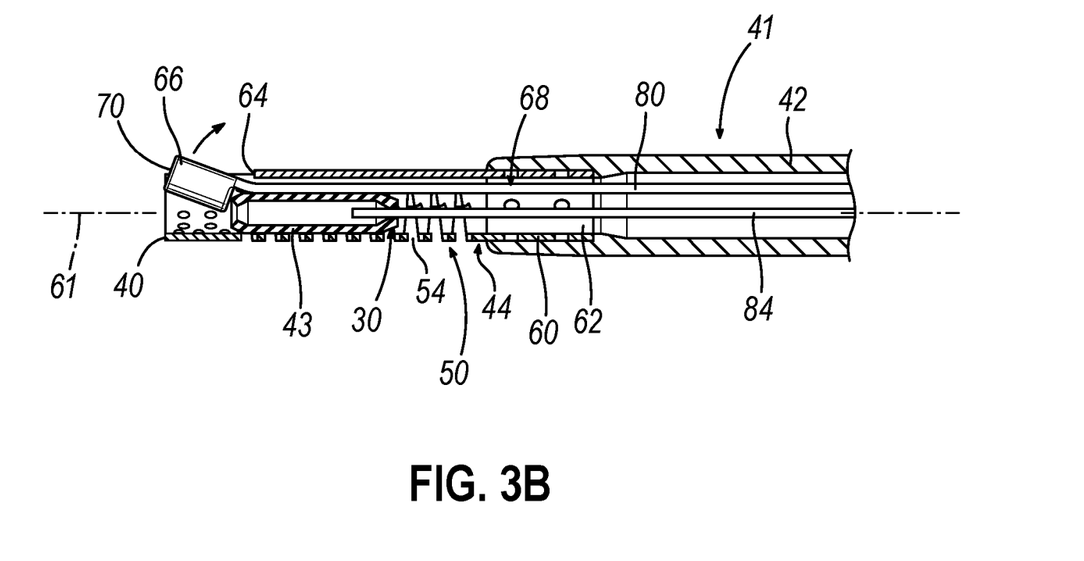
FIG. 3B depicts the cross-sectional view of the dilation instrument similar to FIG. 3A, but shows the enlarged portion of the dilation catheter urging the distal head of the endoscope through the clearance opening and toward the deflected state.

FIGS. 3A-3B show one example of endoscope (68) and dilation catheter (30) having various diameters longitudinally positioned therealong and configured to cooperate with clearance opening (64) in order to translate dilator (43) passed distal head (66). More particularly, distal head (66) of endoscope (68) defines a head diameter transverse to central axis (61) and elongate endoscope body (80) defines an endoscope body diameter transverse to central axis (61) and smaller than head diameter. Similarly, dilator (43) of dilation catheter (30) defines a dilator diameter transverse to central axis (61) and elongate catheter body (84) defines a catheter body diameter transverse to central axis (61) and smaller than dilator diameter. Guide lumen (62) is sized to have a lumen diameter transverse to central axis (61) generally larger than a collective sum of endoscope body diameter and dilator diameter such that dilator (43) selectively translates alongside elongate endoscope body (80) within guide lumen (62) during use. In contrast, a collective sum of dilator diameter and head diameter is larger than guide lumen (62). Dilator (43) thus urges distal head (66) to vacate guide lumen (62) through clearance opening (64) when longitudinally aligned therewith to accommodate move of dilation catheter (30) while allowing the operator to distally view the anatomy of the patient directly distal of distal guide end (40) before and after distal placement of dilator (43).

Figure 3C:
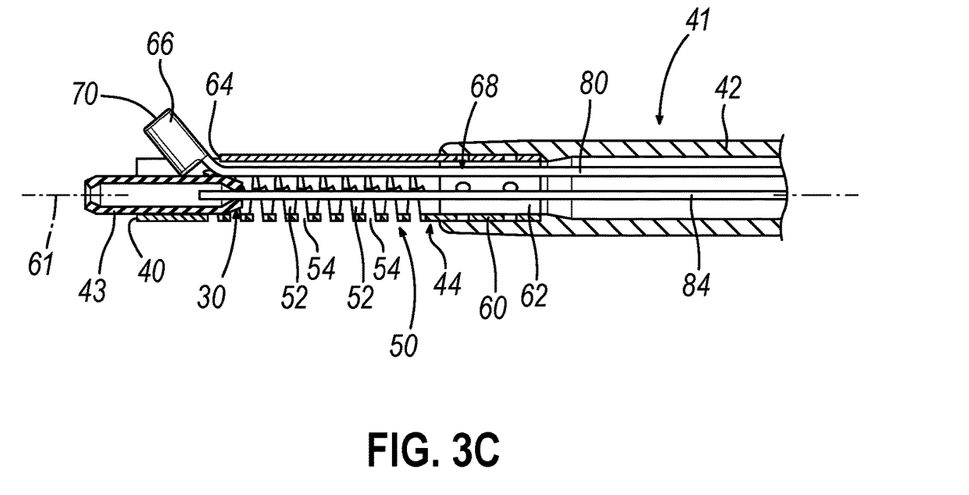
FIG. 3C depicts the cross-sectional view of the dilation instrument similar to FIG. 3B, but shows the distal head of the endoscope in the deflected state as the enlarged portion of the dilation catheter distally passes thereby toward a distal position.
Figure 3D:
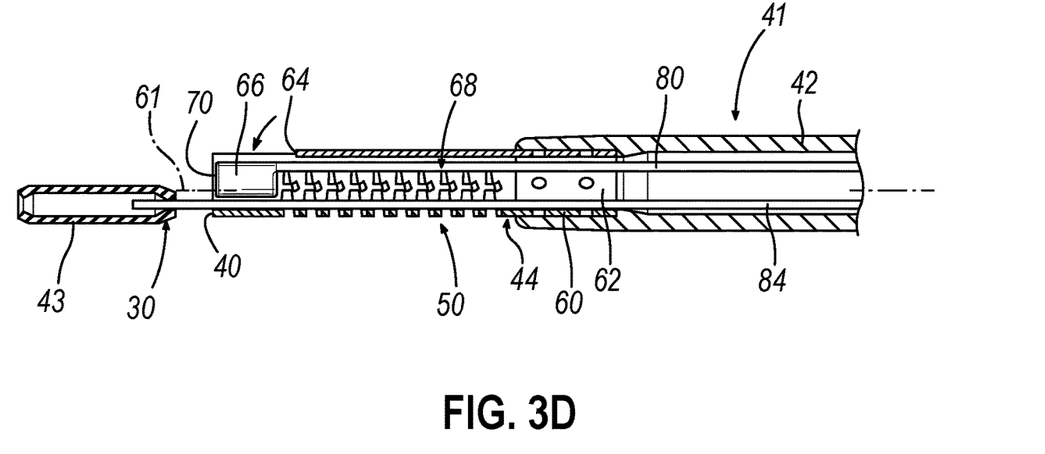
FIG. 3D depicts the cross-sectional view of the dilation instrument similar to FIG. 3C, but shows the enlarged portion of the dilation catheter in the distal position from the distal head of the endoscope as the distal head of the endoscope returns from the deflected state in the clearance opening toward the distal facing use state.

In use, with respect to FIGS. 3A-3B, the operator distally slides dilation catheter (30) radially alongside elongate endoscope body (80) until engaging the proximal portion of distal head (66) in the distal facing use position. A distal portion of dilator (43), in turn, urges distal head (66) to pivot relative to elongate endoscope body (80) into clearance opening (64) from the distal facing use position to the deflected position, thereby at least partially vacating guide lumen (62). Dilator (43) continues to distally translate as shown in FIG. 3C, sliding by distal head (66) while continuing to urge distal head (66) in the deflected position away from central axis (61). As a remaining proximal portion of dilator (43) distally slides by distal head (66), dilator (43) releases distal head (66) such that distal head (66) resiliently returns from the deflected position to the distal facing use position of FIG. 3D. The operator may thus continue viewing the anatomy and dilator (43) directly distal of distal guide end (40) for dilating the anatomy as desired. Once dilation is complete, the operator by proximally reverse dilator (43) to again pivot distal head (66) back and forth through distal facing use and deflected positions to withdrawn dilation catheter (30) back into guide clearance shaft (41). In some versions, the distal and/or proximal end of distal head (66) includes a chamfered surface to promote smooth lateral deflection of distal head (66) as dilator (43) engages distal head (66) during distal and proximal translation of dilator (43).

D. Exemplary Compact Endoscope

Figures 4, 5, 6:
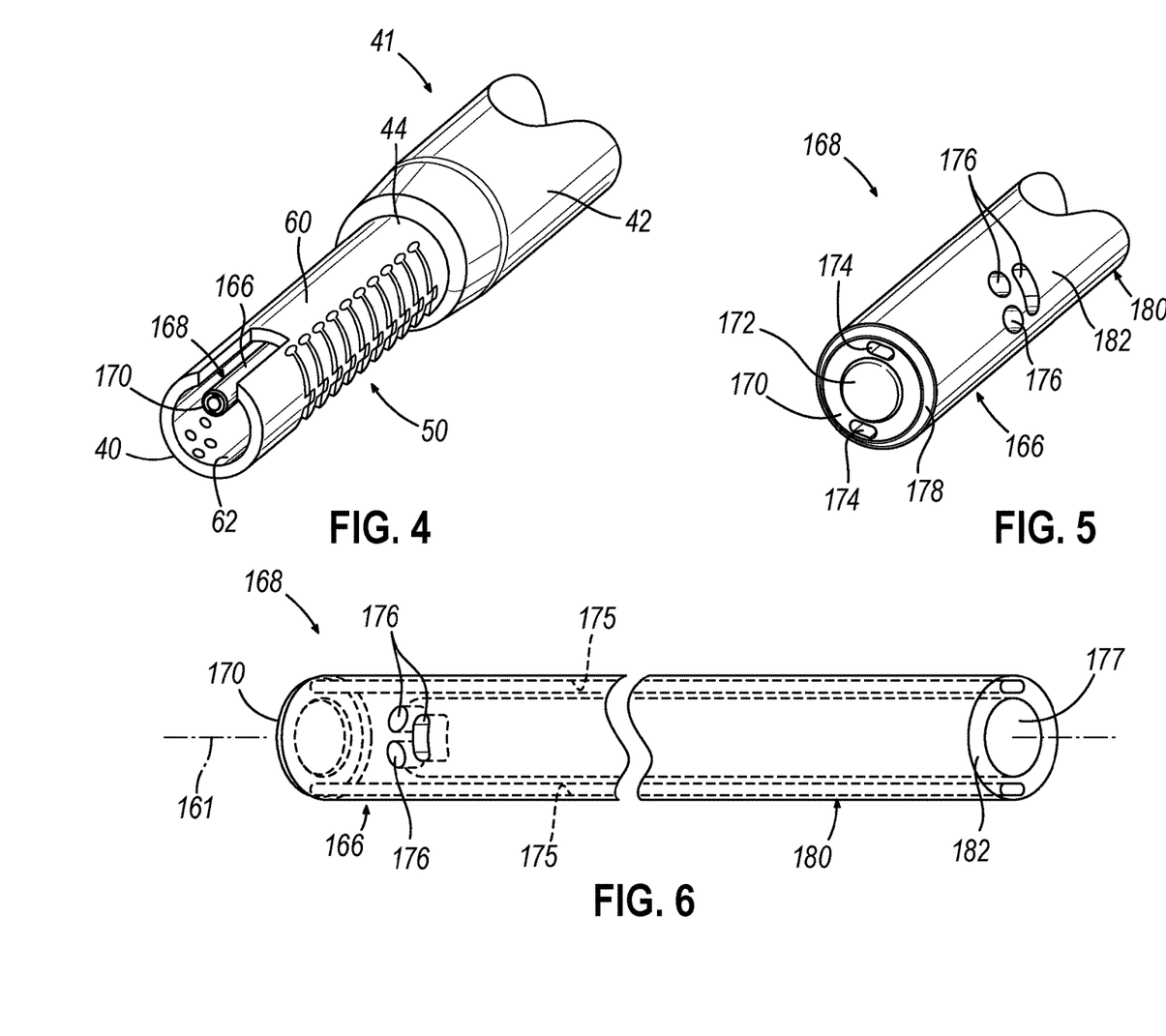
FIG. 4 depicts the clearance shaft of FIG. 2A having a second exemplary endoscope positioned therein.
FIG. 5 depicts an enlarged perspective view of the endoscope of FIG. 4.
FIG. 6 depicts an isometric view of the endoscope of FIG. 4.

FIGS. 4-6 show guide clearance shaft (41) having a second exemplary endoscope (168) positioned within guide lumen (62). As shown in the present example, a distal head (166) of endoscope (168) distally extends to a distal end face (170) having a co-axially positioned camera (172) positioned thereon. In addition, a pair of suction openings (174) of respective suction conduits (175) are positioned on distal end face (170) at one side lateral of camera (172) as well as an opposite lateral side of camera (172). An annular light source (178) surrounds camera (172) at a fillet edge around distal end face (170). Light source (178) is more particularly a light emitting diode in the present example.

An elongate endoscope body (180) is flexible and proximally extends from distal head (166) and includes suction conduits (175) and an irrigation conduit (177) proximally extending therethrough as well as various wires (not shown) communicating power and/or data with light source (178) and camera (172). A plurality of irrigation openings (176) of irrigation conduit (177) extend radially through an annular sidewall (182) of elongate endoscope body (180) to fluidly communicate with irrigation conduit (177) centrally and longitudinally extending through elongate endoscope body (180) along a central axis (161). In contrast, suction conduits (175) are positioned on laterally opposing sides of elongate endoscope body (180) and longitudinally extend through annular sidewall (182) to respective suction openings (174) on distal end face (170). Suction and irrigation conduits (175, 177) are fluidly sealed from each other and configured to fluidly connect to suction and irrigation sources (34, 28) (see FIG. 1A). In the present example, suction openings (174), suction conduits (175), irrigation openings (176), and irrigation conduit (177) are each machined into a unitary structure such that endoscope body (180) with annular sidewall (182) and distal head (166) are formed as a single, unitary structure having annular light source (178) and camera (172) attached thereto. In other examples, a plurality of components may be assembled into an alternative elongate endoscope body (not shown) with one or more of such suction openings (174), suction conduits (175), irrigation openings (176), or irrigation conduit (177) being assembled together. The invention is thus not intended to be unnecessarily limited to the particular, unitary structure of elongate endoscope body (180) as shown in the present example.

In the present example, distal head (166) is relatively compact compared to distal head (66) (see FIG. 2A) and has the same diameter as elongate endoscope body (180), which is shown as the same diameter as elongate endoscope body (80) (see FIG. 3A) discussed above. Arranging suction and irrigation openings (174, 176) as well as suction and irrigation conduits (175, 177) as shown in FIGS. 4-6 enables compactness of distal head (166) in order to longitudinally slide dilator (43) (see FIG. 3A) by distal head (166) without deflecting distal head (166). In other words, distal head (166) of endoscope (168) and dilator (43) (see FIG. 3A) may be positioned radially side-by-side in longitudinal alignment within guide lumen (62) without at least some portion of distal head (166) vacating guide lumen (62). While endoscope (168) is shown in the present example within guide clearance shaft (41), it will be appreciated that endoscope (168) may be used with any such dilation catheter, such as dilation catheter (30) (see FIG. 1A) discussed above, or any shaft assembly with or without clearance opening (64) (see FIG. 2A).

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) an instrument body; (b) a guide shaft distally projecting from the instrument body along a central axis, including: (i) a guide sidewall surrounding the central axis, (ii) a guide lumen defined by the guide sidewall, and (iii) a clearance opening radially extending through the guide sidewall in communication with the guide lumen; and (c) a first surgical tool, including: (i) an elongate body at least partially positioned within the guide lumen, and (ii) a distal head extending from the elongate body proximate to the clearance opening, wherein the distal head is configured to deflect relative to the elongate body from a first position to a second position, wherein the distal head in the first position is positioned within the guide lumen along the central axis, and wherein the distal head in the second position is deflected from the central axis and extends at least partially through the clearance opening thereby vacating at least a portion of the guide lumen for introducing a second surgical tool through the guide lumen.

Example 2

The surgical instrument of Example 1, wherein the elongate body defines a body diameter transverse to the central axis, wherein the distal head defines a head diameter transverse to the central axis, and wherein the head diameter is larger than the body diameter.

Example 3

The surgical instrument of any one or more of Examples 1 through 2, wherein the guide sidewall distally extends to a distal shaft end of the guide shaft, wherein the distal head is proximally positioned relative to the distal shaft end in the second position.

Example 4

The surgical instrument of Example 3, wherein the distal head is proximally positioned relative to the distal shaft end in the first position

Example 5

The surgical instrument of Example 4, wherein the clearance opening distally extends to the distal shaft end.

Example 6

The surgical instrument of any one or more of Examples 1 through 5, wherein the guide sidewall distally extends to a distal shaft end of the guide shaft, and wherein the clearance opening distally extends to the distal shaft end.

Example 7

The surgical instrument of any one or more of Examples 1 through 6, wherein the first surgical tool is an endoscope, and wherein the distal head of the endoscope includes a camera.

Example 8

The surgical instrument of Example 7, wherein the distal head of the endoscope further includes an irrigation opening configured to discharge a fluid therefrom and a suction opening configured to receive a fluid therein.

Example 9

The surgical instrument of Example 7, further comprising a second surgical tool slidably positioned within the guide lumen having an enlarged portion and a narrowed portion, wherein the enlarged portion is configured to urge the distal head of the endoscope toward the second position upon longitudinal alignment therewith, and wherein the narrowed portion is configured concurrently be positioned alongside the distal head of the endoscope in the first position upon longitudinal alignment therewith.

Example 10

The surgical instrument of Example 9, wherein the second surgical tool is a dilation catheter.

Example 11

The surgical instrument of any one or more of Examples 1 through 10, further comprising a second surgical tool slidably positioned within the guide lumen having an enlarged portion and a narrowed portion, wherein the enlarged portion is configured to urge the distal head of the first surgical tool toward the second position upon longitudinal alignment therewith, and wherein the narrowed portion is configured concurrently be positioned alongside the distal head of the first surgical tool in the first position upon longitudinal alignment therewith.

Example 12

The surgical instrument of Example 11, wherein the second surgical tool is a dilation catheter.

Example 13

The surgical instrument of any one or more of Examples 1 through 12, wherein the distal head is pivotally mounted relative to the guide sidewall of the guide shaft, and wherein the distal head is configured to pivot from the first position toward the second position.

Example 14

The surgical instrument of any one or more of Examples 1 through 13, wherein the guide sidewall defines an outer profile transverse to the central axis, and wherein the distal head of the first surgical tool is positioned within the outer profile in the first position.

Example 15

The surgical instrument of any one or more of Examples 1 through 14, wherein the guide shaft includes a flexible distal portion and a rigid proximal portion, wherein the flexible distal portion is configured to deflect relative to the rigid proximal portion with the distal head of the first surgical tool contained therein.

Example 16

A surgical instrument, comprising: (a) an endoscope, including: (i) a proximal end portion proximally extending to a proximal end face, (ii) a distal end portion distally extending to a distal end face, and (iii) an elongate body longitudinally extending along a central axis, having: (A) an annular sidewall surrounding the central axis extending from the proximal end face to the distal end face, (B) a first suction conduit configured to fluidly connect to a vacuum source and communicate a vacuum proximally therethrough, (C) an irrigation conduit configured to fluidly connect to an irrigation fluid source and communicate an irrigation fluid distally therethrough, (iv) a first suction opening extending through the distal end face and fluidly connected to the first suction conduit, (v) a first irrigation opening extending through the annular sidewall at the distal end portion and fluidly connected to the first suction conduit, and (vi) a camera secured to the distal end face.

Example 17

The surgical instrument of Example 16, further comprising a light source secured to the distal end face.

Example 18

The surgical instrument of Example 17, further comprising a second suction opening extending through the distal end face and configured to fluidly connect to a second suction conduit in the elongate body.

Example 19

The surgical instrument of any one or more of Examples 16 through 18, further comprising: (a) an instrument body;

(b) a dilation catheter configured to selectively move relative to the instrument body; and (c) a guide shaft distally projecting from the instrument body, including: (i) a guide sidewall, and (ii) a guide lumen defined by the guide sidewall, wherein the endoscope is configured to be concurrently positioned radially adjacent to the dilation catheter within the guide lumen.

Example 20

A method of concurrently accommodating a first surgical tool and a second surgical tool within a guide lumen of a surgical instrument, wherein the surgical instrument includes (a) an instrument body; (b) a guide shaft distally projecting from the instrument body along a central axis, including: (i) a guide sidewall surrounding the central axis, (ii) the guide lumen defined by the guide sidewall, and (iii) a clearance opening radially extending through the guide sidewall in communication with the guide lumen; and (c) the first surgical tool, including: (i) an elongate body at least partially positioned within the guide lumen, and (ii) a distal head extending from the elongate body proximate to the clearance opening, wherein the distal head is configured to deflect relative to the elongate body from a first position to a second position, wherein the distal head in the first position is positioned within the guide lumen along the central axis, and wherein the distal head in the second position is deflected from the central axis and extends at least partially through the clearance opening thereby vacating at least a portion of the guide lumen, the method comprising: (a) engaging the second surgical tool against the distal head of the first surgical tool to thereby urge the distal head of the first surgical tool from the first position to the second position and concurrently accommodate both of the first and second surgical tools within the guide lumen.

III. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) an instrument body;
   (b) a guide shaft distally projecting from the instrument body along a central axis, including:
      (i) a guide sidewall surrounding the central axis,
      (ii) a guide lumen defined by the guide sidewall, and
      (iii) a clearance opening radially extending through the guide sidewall in communication with the guide lumen;
   (c) a first surgical tool, including:
      (i) an elongate body at least partially positioned within the guide lumen, and
      (ii) a distal head extending from the elongate body proximate to the clearance opening, the distal head being configured to deflect relative to the elongate body from a first position to a second position; and (d) a second surgical tool slidably positioned within the guide lumen, the second surgical tool including:
   (i) an enlarged portion, and
   (ii) a narrowed portion,
   the distal head, in the first position, being positioned within the guide lumen along the central axis,
   the distal head, in the second position, being deflected from the central axis such that the distal head is obliquely oriented relative to the central axis, the distal head, in the second position, extending at least partially through the clearance opening thereby vacating at least a portion of the guide lumen for introducing the second surgical tool through the guide lumen, and
   the enlarged portion of the second surgical tool being configured to urge the distal head of the first surgical tool toward the second position upon longitudinal alignment between the enlarged portion of the second surgical tool and the distal head of the first surgical tool.

2. The surgical instrument of claim 1, the elongate body defining a body diameter transverse to the central axis, the distal head defining a head diameter transverse to the central axis, and the head diameter being larger than the body diameter.

3. The surgical instrument of claim 1, the guide sidewall distally extending to a distal shaft end of the guide shaft, the distal head being proximally positioned relative to the distal shaft end in the second position.

4. The surgical instrument of claim 3, the distal head being proximally positioned relative to the distal shaft end in the first position.

5. The surgical instrument of claim 4, the clearance opening distally extending to the distal shaft end.

6. The surgical instrument of claim 1, the guide sidewall distally extending to a distal shaft end of the guide shaft, and the clearance opening distally extending to the distal shaft end.

7. The surgical instrument of claim 1, the first surgical tool being an endoscope, and the distal head of the endoscope including a camera.

8. The surgical instrument of claim 7, the distal head of the endoscope further including an irrigation opening configured to discharge a fluid therefrom and a suction opening configured to receive a fluid therein.

9. The surgical instrument of claim 7, the narrowed portion being configured to concurrently be positioned alongside the distal head of the endoscope in the first position upon longitudinal alignment therewith.

10. The surgical instrument of claim 9, the second surgical tool being a dilation catheter.

11. The surgical instrument of claim 1, the narrowed portion being configured to concurrently be positioned alongside the distal head of the first surgical tool in the first position upon longitudinal alignment therewith.

12. The surgical instrument of claim 11, the second surgical tool being a dilation catheter.

13. The surgical instrument of claim 1, the distal head being pivotally mounted relative to the guide sidewall of the guide shaft, and the distal head being configured to pivot from the first position toward the second position.

14. The surgical instrument of claim 1, the guide sidewall defining an outer profile transverse to the central axis, and the distal head of the first surgical tool being positioned within the outer profile in the first position.

15. The surgical instrument of claim 1, the guide shaft including a flexible distal portion and a rigid proximal portion, the flexible distal portion being configured to deflect relative to the rigid proximal portion with the distal head of the first surgical tool contained therein.

16. A method of concurrently accommodating a first surgical tool and a second surgical tool within a guide lumen of a surgical instrument, the method comprising:
   (a) providing the surgical instrument including
      (a) an instrument body;
      (b) a guide shaft distally projecting from the instrument body along a central axis, including: (i) a guide sidewall surrounding the central axis, (ii) the guide lumen defined by the guide sidewall, and (iii) a clearance opening radially extending through the guide sidewall in communication with the guide lumen; and
      (c) the first surgical tool, including: (i) an elongate body at least partially positioned within the guide lumen, and (ii) a distal head extending from the elongate body proximate to the clearance opening, the distal head being configured to deflect relative to the elongate body from a first position to a second position, the distal head in the first position being positioned within the guide lumen along the central axis, and the distal head in the second position being deflected from the central axis and extends at least partially through the clearance opening thereby vacating at least a portion of the guide lumen; and
   (b) engaging the second surgical tool against the distal head of the first surgical tool to thereby urge the distal head of the first surgical tool from the first position to the second position and concurrently accommodate both of the first and second surgical tools within the guide lumen, the distal head being parallel with the central axis in the first position, the distal head being oriented obliquely relative to the central axis in the second position.

17. A surgical instrument, comprising:
(a) an instrument body;
(b) a guide shaft distally projecting from the instrument body along a central axis, including:
   (i) a guide sidewall surrounding the central axis,
   (ii) a guide lumen defined by the guide sidewall, and
   (iii) a clearance opening radially extending through the guide sidewall in communication with the guide lumen; and
(c) a first surgical tool, including:
   (i) an elongate body at least partially positioned within the guide lumen, and
   (ii) a distal head extending from the elongate body proximate to the clearance opening, the distal head being configured to deflect relative to the elongate body from a first position to a second position;
   the distal head, in the first position, being positioned within the guide lumen along the central axis,
   the distal head, in the second position, being deflected from the central axis such that the distal head is obliquely oriented relative to the central axis and vacates at least a portion of the guide lumen for introducing a second surgical tool through the guide lumen.

18. The surgical instrument of claim 17, further comprising the second surgical tool, the second surgical tool comprising an enlarged portion.

* * * * *